US005856295A

United States Patent [19]

Sell

[11] Patent Number: 5,856,295

[45] Date of Patent: Jan. 5, 1999

[54] FRAGRANCE MATERIAL

[75] Inventor: Charles Stanley Sell, Woodlands Smeeth, Great Britain

[73] Assignee: Quest International B.V., Naarden, Netherlands

[21] Appl. No.: 913,483

[22] PCT Filed: Mar. 7, 1996

[86] PCT No.: PCT/EP96/01098

§ 371 Date: Sep. 17, 1997

§ 102(e) Date: Sep. 17, 1997

[87] PCT Pub. No.: WO96/30470

PCT Pub. Date: Oct. 3, 1996

[30] Foreign Application Priority Data

Mar. 25, 1995 [EP] European Pat. Off. ................ 9510441

[51] Int. Cl.[6] ...................................................... A61K 7/46

[52] U.S. Cl. ................................................ 512/21; 512/20

[58] Field of Search ......................................... 512/20, 21

[56] References Cited

U.S. PATENT DOCUMENTS

| | | | |
|---|---|---|---|
| 4,283,508 | 8/1981 | Maender | 525/351 |
| 4,469,874 | 9/1984 | Maender | 548/475 |
| 5,360,924 | 11/1994 | Beller et al. | 560/55 |

*Primary Examiner*—José G. Dees
*Assistant Examiner*—Michael A. Williamson
*Attorney, Agent, or Firm*—Pillsbury Madison & Sutro LLP

[57] ABSTRACT

The amide N-ethyl-N-(3-methylphenyl)propionamide has been found to have attractive fragrance characteristics of the woody, vetiver type and so is used for imparting useful fragrance properties to fragrance compositions and to fragranced products.

7 Claims, 1 Drawing Sheet

Figure 1:
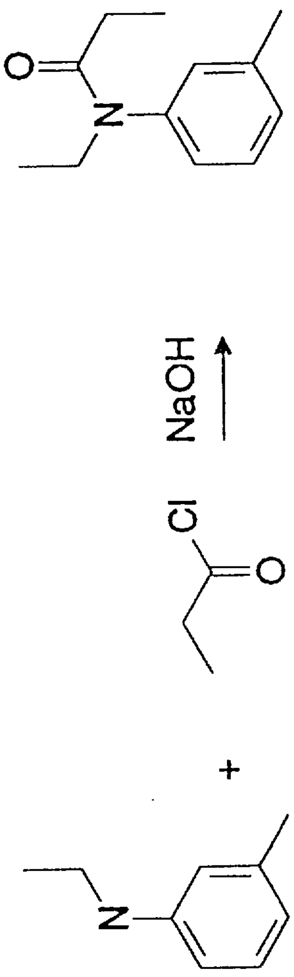

N-ethyl-m-toluidine    propionyl chloride    N-Ethyl-N-(3-methylphenyl)propionamide N-ethyl-m-toluidine propionyl chloride N-Ethyl-N-(3-methylphenyl)propionamide

FRAGRANCE MATERIAL

This application is the national phase of international application PCT/EP96/01098, filed Mar. 7, 1996 which designated the U.S.

FIELD OF INVENTION

This invention concerns the use of an amide as a fragrance material.

BACKGROUND TO THE INVENTION

N-Ethyl-N-(3-methylphenyl)propionamide is a known chemical compound. Although it is not recorded in Chemical Abstracts nor is it in Beilsteins's Handbuch, it is included (under the alternative chemical name m-propiono-toluamide, N-ethyl) in a single line entry as one of many thousands of entries in the US Department of Agriculture's Agriculture Handbook No. 69 issued May 1954 entitled "Chemicals Evaluated as Insecticides and Repellents at Orlando, Fla." In this handbook, this amide is reported to have insect repellent properties. However, the compound has so far never been put to practical use a an insect repellent.

Some amides are known to have useful organoleptic properties. Thus, N-methyl-N-phenyl-2-ethylbutyramide is described in NL-A-7210523 as being useful as a fragrance and flavour material and having a grapefruit-like odour note.

OUTLINE OF THE INVENTION

It has now been found that N-ethyl-N-(3-methylphenyl)-propionamide has interesting organoleptic properties. Thus, in one aspect the invention provides use of N-ethyl-N-(3-methylphenyl)propionamide in fragrance compositions.

In another aspect the invention provides use of N-ethyl-N-(3-methylphenyl)propionamide for imparting useful fragrance properties to a fragranced product.

Furthermore an aspect of the invention are fragrance compositions comprising an olfactively effective amount of N-ethyl-N-(3-methylphenyl)propionamide.

Also within the scope of the invention is a process for preparing fragrance compositions comprising adding to known fragrance materials an olfactively effective amount of N-ethyl-N-(3-methylphenyl)propionamide.

A fragrance composition means a composition comprising various fragrance materials, and optionally a solvent, formulated to have certain useful fragrance characteristics. In most cases fragrance compositions are formulated to have a fragrance generally considered at least inoffensive and preferably pleasing to intended users of the composition. Fragrance compositions are used for imparting a desired odour to the skin and/or any product for which an agreeable odour is indispensable or desirable. Examples of such products are personal and household products including fabric washing powders, washing liquids, fabric softeners and other fabric care products; detergents and household cleaning, scouring and disinfection products; air fresheners, room sprays and pomanders; fine fragrances; soaps, bath and shower gels, shampoos, hair conditioners and other personal cleansing products; cosmetics such as creams, ointments, toilet waters, preshave, aftershave, skin- and other lotions, talcum powders, body deodorants and antiperspirants etc. Fragrance compositions are also used in products that would normally have an unattractive or offensive odour to mask this odour and produce an odour that is less unattractive or offensive. Products in this category include fuel odorants.

The (pleasing) fragrance characteristics may be the main function of the product in which the fragrance compositions has been incorporated, as in the case of a fine fragrance, or may be ancillary to the main function of the product, as e.g. in the case of detergents, cleaning products and skin care products.

The amide of the invention has attractive fragrance characteristics. The odour type is woody, vetiver-like, agarwood (or oud wood), Cashmeran (Cashmeran is a Trade Mark) and spicy with a grapefruit top note. The amide of the invention has good odour tenacity, and lasts more than 24 hours on smelling strip. Thus, the woody, vetiver-like, and agarwood odour notes are of particular importance.

The fragrance characteristics of the amide of the invention mean that it finds potential application as a fragrance material in a wide range of fragrance compositions and fragranced products, including those noted above. The woody vetiver-like odour means that it is particularly useful in fine fragrances.

Also, although the amide has never found any practical use as insect repellent as such, it synergistically provides useful insect repellent properties to fragrance compositions in which it is comprised or enhances such properties already present due to other components in the fragrance composition.

Other fragrance materials which can be advantageously combined with the amide according to the invention in a fragrance composition are, for example, natural products such as extracts, essential oils, absolutes, resinoids, resins, concretes etc., but also synthetic materials such as hydrocarbons, alcohols, aldehydes, ketones, ethers, acids, esters, acetals, ketals, nitrites, etc., including saturated and unsaturated compounds, aliphatic, carbocyclic and heterocyclic compounds.

Such fragrance materials are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA.

Examples of fragrance materials which can be used in combination with the amide according to the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzyl-carbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl) propanal, 2-methyl-3-(p-isopropyl-phenyl)propanal, 3-(p-tert-butylphenyl)-propanal, 2,4-dimethylcyclohex-3-enyl-carboxaldehyde, tricyclodecenyl acetate, tricyclodecenyl propionate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyltetrahydropyran, 3-carboxymethyl-2-pentyl-cyclopentane, 2-n-heptylcyclopentanone, 3-methyl-2-pentyl-2-cyclopentenone, n-decanal, n-dodecanal, 9-decenol-1, phenoxyethyl isobutyrate, phenyl-acetaldehyde dimethyl-acetal, phenylacetaldehyde diethylacetal, geranyl nitrile, citronellyl nitrile, cedryl acetate, 3-isocamphyl-cyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks tetralin musks isochroman musks macrocyclic ketones, macrolactone musks, ethylene brassylate.

Solvents which can be used for fragrance compositions which contain the amide according to the invention are, for example: ethanol, isopropanol, diethyleneglycol monoethyl ether, dipropylene glycol, diethyl phthalate, triethyl citrate, isopropyl myristate, etc.

The quantities in which the amide according to the invention can be used in fragrance compositions or in fragranced products may vary within wide limits and depend, inter alia, on the nature of the product, on the nature and the quantity of the other components of the fragrance composition in which the amide is used and on the olfactive effect desired. It is therefore only possible to specify wide limits, which, however, provide sufficient information for the specialist in the art to be able to use the amide according to the invention for his specific purpose. In fragrance compositions an amount of 0.0% by weight or more of the amide according to the invention will generally have a perceptible olfactive effect. Preferably the amount is at least 0.1% by weight, more preferably at least 1%. The amount of the amide according to the invention present in fragranced products will generally be at least 10 ppm by weight, preferably at least 100 ppm, more preferably at least 1000 ppm.

The amide may be used in fragrance compositions in an amount of up to about 80% by weight.

The amide of the invention is conveniently prepared by acylation of N-ethyl-m-toluidine with propionyl chloride in a generally conventional reaction. For manufacturing purposes it may be preferable to use a propionate ester instead of propionyl chloride as the acylating species. The amide can be produced relatively cheaply compared to many other known fragrance chemicals, and so provides a useful, stable, and easily accesible fragrance material, particularly for the fine fragrance market.

The invention will be further described, by way of illustration, in the following examples and with reference to the accompanying drawings in which FIG. 1 shows the reaction scheme for preparation of the amide of the invention.

EXAMPLE 1

N-Ethyl-N-(3-methylphenyl)propionamide was prepared on a laboratory scale by acylation of N-ethyl-m-toluidine with propionyl chloride. The reaction was carried out in a 5 litre 3 necked round bottomed flask equipped with a mechanical stirrer, a thermometer (0°–250° C.), an addition vessel and a condenser.

Stage 1

N-Ethyl-m-toluidine (ex Aldrich) was distilled through a vigreux column to give a clear liquid distillate for use in the second stage.

Stage 2

Sodium hydroxide (196 g, 2.2 mole) was dissolved in water (2 ltr) and the solution added to the flask. Distilled N-Ethyl-m-toluidine (270 g, 2.0 mole) in toluene (1 ltr) was added to the hydroxide solution and the mix stirred slowly at 30° C. Propionyl chloride (186 g, 2.0 mole) was then added from the addition vessel during 30 mins. During the addition the temperature rose slowly to 70° C. The reaction mix was then stirred for a further 2 hrs and allowed to cool to ambient temperature before being poured into a 5 ltr separating flask. The lower aqueous phase was run off and discarded. The organic phase was washed with hydrochloric acid solution (2×2 ltr 1.0 molar aqueous) and water (2×2 ltr), then dried using magnesium sulphate, filtered and the toluene removed under vacuum using a rotary evaporator.

The crude product (315 g) was then fractionated using a 60 cm Sulzer (Sulzer is a Trade Mark) packed column. Fractions b.pt 101°–103° C. at 4.0 mb were collected. After a total of 212.5 g had been distilled, the pot residue began to solidify and the fractionation was terminated. After cooling, the residue was weighed (102 g).

The distilled product was analysed by capillary gas chromatography (SE 54) and found to be 99.5% pure.

EXAMPLE 2

A hyacinth/woody type fragrance composition was prepared according to the following recipe:

| | % w/w |
|---|---|
| Phenylacetaldehyde 50% in diethyl phthalate | 37 |
| Phenyl-ethyl alcohol | 10 |
| Benzyl acetate | 10 |
| Heliotropin | 10 |
| Linalol | 5 |
| Clove Bud Oil | 5 |
| Product of Example 1 | 23 |
| | 100 |

I claim:

1. Fragrance compositions comprising known fragrance materials and in addition comprising an olfactively effective amount of N-ethyl-N-(3-methylphenyl)-propionamide.

2. Fragrance compositions according to claim 1 comprising at least 0.01% by weight of N-ethyl-N-(3-methylphenyl) -propionamide.

3. Fragrance compositions according to claim 2 comprising at least 0.1% by weight of N-ethyl-N-(3-methylphenyl) -propionamide.

4. Fragranced product comprising an olfactively effective amount of N-ethyl-N-(3-methylphenyl)propionamide.

5. Fragranced product according to claim 4 comprising at least 10 ppm of N-ethyl-N-(3-methylphenyl)propionamide.

6. Fragranced product according to claim 5 comprising at least 100 ppm of N-ethyl-N-(3-methylphenyl)-propionamide.

7. A process for preparing a fragrance composition comprising known fragrance materials which comprises the step of adding thereto an olfactively effective amount of N-ethyl-N-(3-methylphenyl) propionamide.

* * * * *